United States Patent [19]

Gupte et al.

[11] Patent Number: 5,676,130
[45] Date of Patent: Oct. 14, 1997

[54] SEPARATOR FOR POWDERED INHALERS

[75] Inventors: Arun Rajaram Gupte; Heinrich Kladders, both of Ingelheim, Germany

[73] Assignee: Boehringer Ingelheim GmbH, Inc., Ingelheim am Rhein, Germany

[21] Appl. No.: 618,475

[22] Filed: Mar. 18, 1996

Related U.S. Application Data

[63] Continuation of Ser. No. 295,901, filed as PCT/EP93/00582 published as WO93/18811 Sep. 30, 1993, abandoned.

[30] Foreign Application Priority Data

Mar. 19, 1992 [DE] Germany .......... 42 08 880.1

[51] Int. Cl.⁶ .................................. A61M 15/00
[52] U.S. Cl. .................. 128/203.19; 128/200.14; 128/200.18; 128/203.12; 128/203.15
[58] Field of Search .............. 128/200.11, 200.14, 128/200.18, 200.21, 200.23, 203.12, 203.15, 203.19, 203.24

[56] References Cited

U.S. PATENT DOCUMENTS

| 2,906,463 | 9/1959 | Curry .................. 128/200.18 |
| 3,236,458 | 2/1966 | Ramis ................. 128/200.18 |
| 3,522,806 | 8/1970 | Szekely ............... 128/200.18 |
| 3,795,244 | 3/1974 | Lax et al. ........... 128/203.15 |
| 3,807,400 | 4/1974 | Cocozza ............. 128/203.15 |
| 3,838,686 | 10/1974 | Szekely ............. 128/200.18 |
| 4,570,630 | 2/1986 | Elliott et al. ........ 128/203.15 |
| 4,739,754 | 4/1988 | Shaney .............. 128/203.15 |
| 4,796,614 | 1/1989 | Nowacki et al. ..... 128/200.14 |
| 4,940,051 | 7/1990 | Lankinen ........... 128/200.18 |
| 5,054,478 | 10/1991 | Grychowski et al. .. 128/200.14 |

FOREIGN PATENT DOCUMENTS

| 0645004 | 9/1962 | Italy ................... 128/200.18 |
| 9204065 | 3/1992 | WIPO ............... 128/200.18 |
| 9204070 | 3/1992 | WIPO ............... 128/200.18 |
| 9210228 | 6/1992 | WIPO ............... 128/200.18 |

Primary Examiner—Vincent Millin
Assistant Examiner—V. Srivastava
Attorney, Agent, or Firm—R. P. Raymond; M-E. M. Devlin; A. R. Stempel

[57] ABSTRACT

A separator for attachment to devices for administration of powders into the lungs, which separator separates particles to be inhaled into the lungs from other particles in the powders.

8 Claims, 3 Drawing Sheets 5,676,130

SEPARATOR FOR POWDERED INHALERS

This is a continuation of application Ser. No. 08/295,901, filed as PCT/EP93/00582 Mar. 13, 1993 published as WO93/18811 Sep. 30, 1993 now abandoned.

BACKGROUND OF THE INVENTION

1. Field of the Invention

The invention relates to a separator which is intended to be added on to devices for powder inhalation and which serves to separate the particles which are not bound for the lungs from the inhalable particles in the aerosol produced by such devices.

2. Description of the Related Art

In inhalation therapy of respiratory diseases it is necessary for the powdered drugs to reach the desired activity site in the lungs. This is particularly important with the corticosteroids, which are increasingly administered by inhalation. If the drugs are deposited in the oropharyngeal cavity, the risk of side effects, particularly local side effects, is considerable.

The known powder inhalers are only able to deliver a certain amount of active substance in such fine form (inhalable dose) that it is able to penetrate deeply enough into the lungs. Coarse particles which are frequently produced by the clumping of the micronised powdered drug are deposited in the oropharyngeal cavity, however.

SUMMARY OF THE INVENTION

The present invention solves the problem of providing a device which comminutes and/or separates off the coarser particles during the inhalation of aerosols and allows primarily only the particles destined for the lungs to pass through.

The essential element of such a separator is a chamber having means by which the aerosol is guided in such a way that the coarser powder fractions are deposited and/or comminuted, and which has a device for attachment to the inhaler as well as a mouthpiece.

DETAILED DESCRIPTION OF THE DRAWINGS

Figure 1:
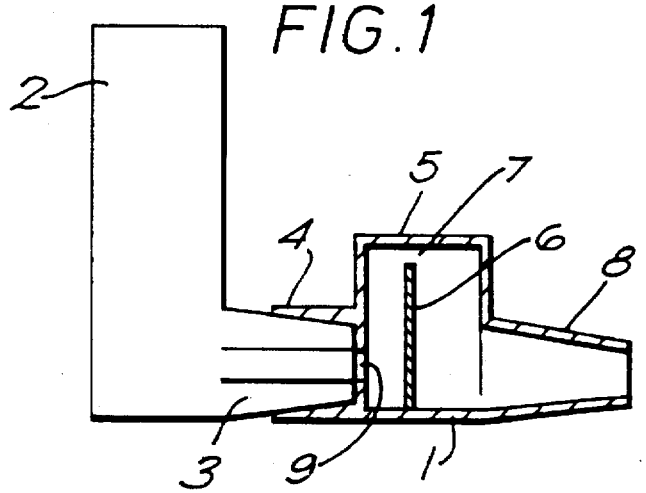
FIGS. 1 to 11 show separators of the construction according to the invention and details thereof, illustrated diagrammatically (in the position of use, unless otherwise specified).

FIG. 1 shows a longitudinal section through a separator of this kind with the conventional type inhaler connected thereto.

The separator 1 is fitted onto the inhaler 2 by means of a connector 4 provided for receiving the inhaler mouthpiece 3. The aerosol is directed against the impact plate 6 which is provided in the chamber 5 of the separator transversely to the direction of flow and flows upwardly along said plate 6 so that (in the position of use) it passes above the impact plate 6 through the opening 7 into the rear part of the chamber 5, on into the mouthpiece 8 and from there into the mouth or respiratory tract of the patient. In this embodiment, there is no opening at the side between the wall of the chamber and the impact plate. The impact plate 6 may be provided both in this embodiment and in the alternative versions with means for improving the separating effect, e.g. with ribs of the same or varying height transversely to the air flow, more particularly at the impact end.

For the separator to function properly the dimensions must be matched to one another to some extent. Thus, the spacing between the air inlet opening 9 and the impact plate 6 should be roughly 2 to 12 mm, the height of the impact plate above the highest point of the air inlet opening 9 should be about 10 to 20 mm and the height of the opening 7 should be about 2 to 10 mm with a width of about 10 to 30 mm.

However, these figures should only be taken as a guide, since if the form is changed the dimensions will also be different. Anyone skilled in the art can determine suitable dimensions by simple experiment. It is important for good separation that the air current in the separator, particularly in the region in front of the impact plate 6, is not accelerated too much but is rather slowed down. However, acceleration may be desirable in those aerosols which contain larger particles in the form of relatively loose agglomerates which are broken up if the impact is powerful enough. The resistance to the flow should not be too great; this is because the inhalers are intended for patients whose lung function in many cases is not up to normal levels. Flow cross-sections of more than about 20 $mm^2$ will generally ensure that resistance is not excessive.

Figure 2A:
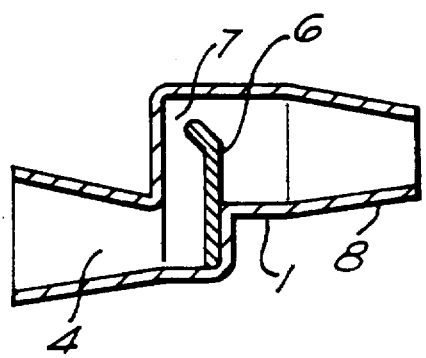
Figure 2B:
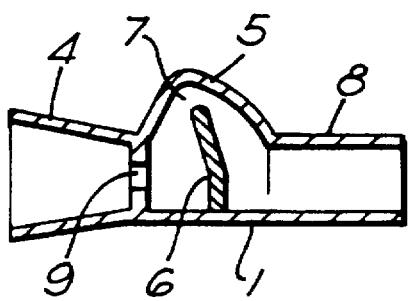
Figure 2C:
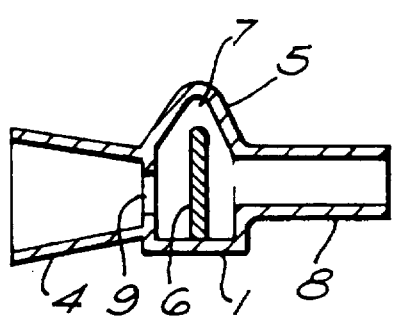
Figure 3:
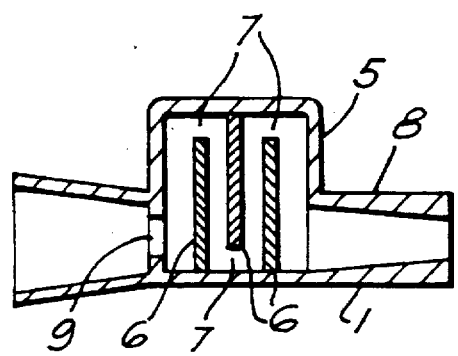
Figure 4:
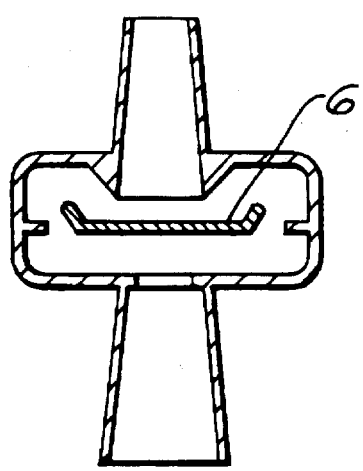
Figure 5:
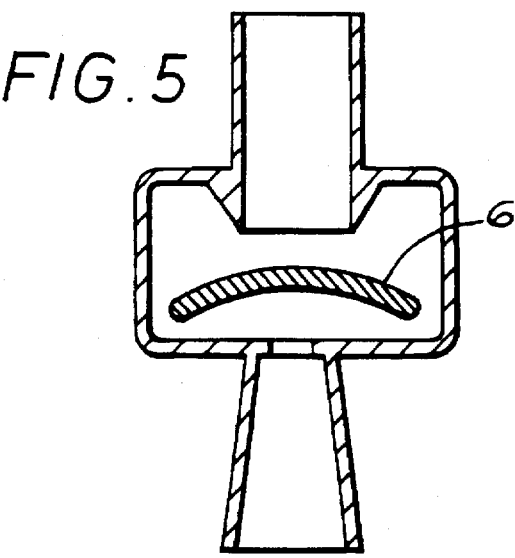

The chamber 5 of the separator may take various forms; its cross-section—perpendicular to the plane of the drawing and parallel to the line A—A'—may for example be round, elliptical, rectangular or polygonal, or even asymmetrical. The section in the plane of the drawing may also take a variety of forms, as illustrated in FIGS. 2a to 2c, for example. The opening 7 may be not only slot-shaped but also round, elliptical, polygonal or sieve-like, but in each case there must be sufficient permeability for the air current. A variety of constructions are possible for the impact wall 6; it may be, for example, curved or angled, as in FIGS. 2a or 2c, and it may also have an uneven surface consisting of bumps, regularly arranged prisms, blocks, pyramids or columns having, for example, polygonal, round or y-shaped cross-section, depressions or transverse grooves or ribs.

Figure 6:
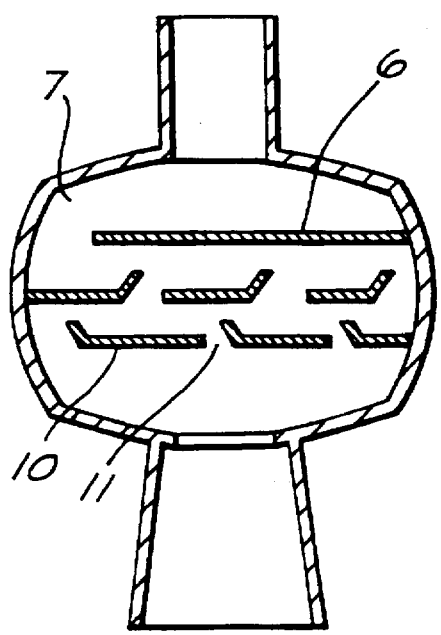

FIGS. 4 to 7 show horizontal sections through other embodiments of the separator according to the invention along the longitudinal axis. In FIG. 6, in front of the impact plate 6 there are baffle elements 10 between which the aerosol is deflected through slot-like openings 11 onto the impact plate 6.

Figure 7:
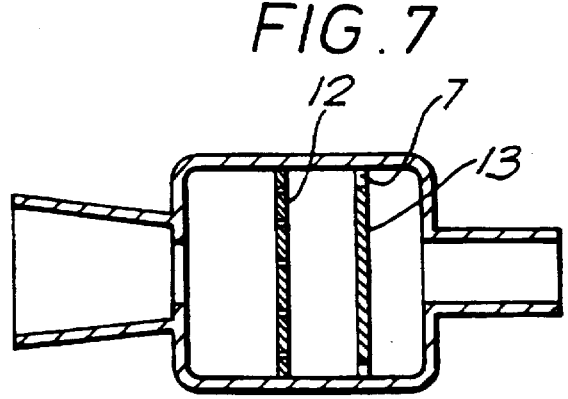

FIG. 7 shows a section along the longitudinal axis of a rotationally symmetrical separator. On entering the chamber the aerosol first hits a perforated plate 12. This may be provided, for example, with about 30 evenly distributed openings having a cross-sectional area of about 1 $mm^2$. The impact plate 13 in this case is a circular disc between whose edge and the wall of the chamber there is an annular gap to act as an opening. The impact plate is connected to the chamber wall or to the perforated plate 12 by one or more fixing elements.

Figure 8:
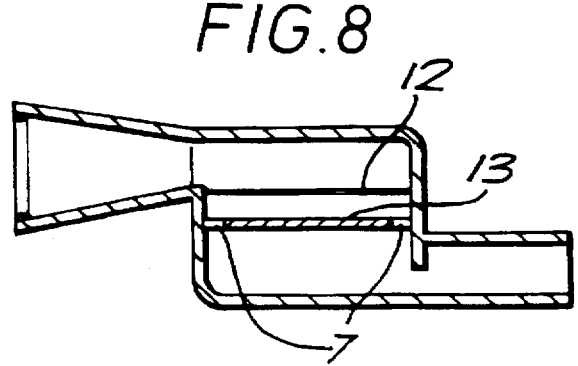

FIG. 8 shows a perpendicular section through a separator in which, as in FIG. 7, a perforated plate 12 and a circular impact plate 13 are provided, although they are horizontally mounted.

Figure 9:
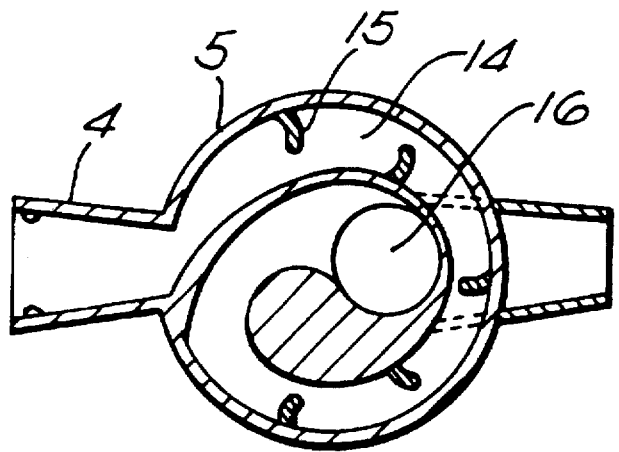
Figure 9A:
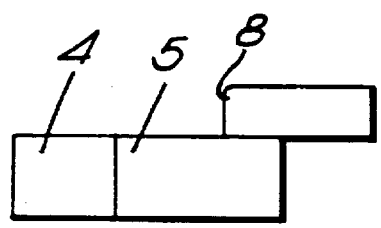
Figure 9B:
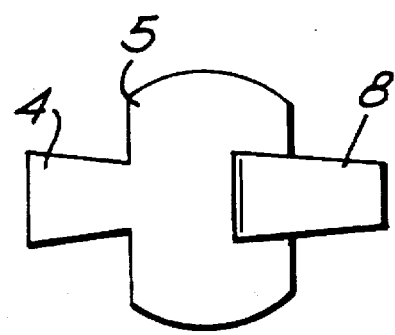

FIG. 9 shows a perpendicular section through a separator in which the aerosol is guided through a spiral channel 14 having a plurality of vane-like impact surfaces 15 and, passes through the outlet 16 into the laterally mounted mouthpiece 8 (FIG. 9a). The spiral channel 14 may, if desired, also be arranged perpendicular to the connector 4 (FIG. 9b).

Figure 10:
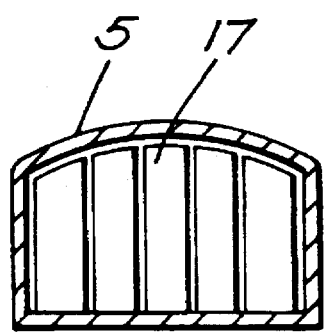
Figure 11:
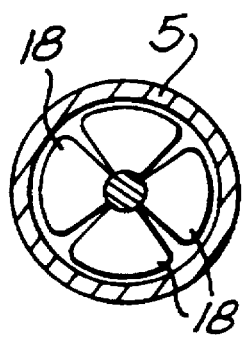

FIG. 10 shows a section perpendicularly through the centre of the chamber 5, at right angles to the direction of flow of the aerosol. Here, the impact surfaces consist of a series of flexible elements 17 which move in the air current in the same way as the reeds in a reed pipe. As shown in FIG. 11, a propeller-like device 18, which may be rotatable or fixed, may also be used as another movable impact element.

DESCRIPTION OF THE PREFERRED EMBODIMENTS

The impact surfaces or impact and deflection elements, perforated plates and flow guides shown in the various embodiments may also, if desired, be put together in different combinations.

For practical purposes it is useful if the separator can be taken apart into its individual components which can be reassembled, and/or if the chamber 5 can be opened by means of a push-on, clamping, flip-open or screw mechanism so that the coarser particles of drug precipitated can be removed from time to time. Between the inhaler and the separator there should be a suitably secured but easily releasable connection. Such a connection may be achieved by methods known per se, e.g. using a simple push-on connection in which a bead or other projections engage in suitable recesses, or a latch, a screw connection of bayonet fitting.

The separator according to the invention is preferably made of plastics but may also consist wholly or partly of metal.

The separator according to the invention may be combined with any inhalers which, when used, produce an aerosol having an undesirable proportion of unwanted, large particles. Therefore, the separator according to the invention may be used in conjunction with devices according to DE-A 1566604, DE-A 3625685, DE-A 3927170, DE-A 4027390, DE-A 4027391, EP-A 166294, EP-A 406893, GB 9026025, PCT/EP 91/01153, WO 90/13328 or U.S. Pat. No. 4,889,114, for example.

A comparison with devices not having a separator shows that the quantity of inhalable powder in the aerosol (particles up to 5.8 μm; "inhalable dose") is not reduced by the separator. However the quantity of coarser particles is reduced to less than one third.

Measurements of this kind may be carried out in a human simulator, i.e. a test arrangement in which the inhaler, with or without the separator, is placed in an air current which approximates to a breath in the quantity and speed of flow.

In the tests mentioned above, for example, an air flow of 28 liters/min were used which was passed through the inhaler for 1.5 seconds on each occasion, whilst the powder for inhalation which was used consisted of fenoterol with an average particle size of 5.8 μm (0.2 mg) on each occasion. The inhalable dose was determined by means of a cascade impactor made by Messrs. Andersen/U.S.A.

We claim:

1. A separator for attachment to a device having a mouthpiece for delivering powdered drugs having varying particle sizes to the lung via inhalation in order to separate from the powdered drug to be inhaled particles that are too large to be deposited in the lung which comprises a connecting means to the mouth piece of the device, a chamber attached to the connecting means having spaced within the chamber one or more deflecting means and at least one of the deflecting means is attached to the chamber, so that an area is created within the chamber for powdered drug to accumulate, and wherein the deflecting means has one or more openings of such size that a particle of powdered drug that can pass through such opening or openings can be deposited with the lung and a mouthpiece attached to the chamber whereby powdered drug flowing from the device into the separator's connecting means, and the separator's chamber impacts upon the deflecting means so that particles above a certain size do not pass through the opening or openings of the deflecting means and such particles accumulate within the chamber of the chamber and into the mouthpiece of the separator.

2. The separator as recited in claim 1 further characterized in that the deflecting means is one or more impact plates attached to the chamber.

3. The separator as recited in claim 2 further characterized in that the opening or openings in the impact plate or plates are one or more slits.

4. The separator as recited in claim 2 further characterized in that the opening or openings in the impact plate or plates are round or elliptical holes.

5. The separator as recited in claim 2 further characterized in that the opening or openings in the impact plate or plates are polygonal holes.

6. The separator as recited in claim 2 further characterized in that the impact plate or plates have uneven surfaces.

7. The separator as recited in claim 2 further characterized in that the impact plate or plates are attached to the chamber at an angle towards the connecting means.

8. The separator as recited in claim 1 further characterized in that the deflecting means is a sieve-like, perforated impact plate and an impact plate, both attached to the chamber.

* * * * *